US00PP33467P2

(12) United States Plant Patent
Dibley

(10) Patent No.: US PP33,467 P2
(45) Date of Patent: Sep. 7, 2021

(54) ***BEGONIA* PLANT NAMED 'BDICP11-0'**

(50) Latin Name: *Begonia rex-cultorum*
Varietal Denomination: BDICP11-0

(71) Applicant: Dibley's Nurseries, Ruthin (GB)

(72) Inventor: Lynne Dibley, Ruthin (GB)

(73) Assignee: Dibley's Nurseries

( * ) Notice: Subject to any disclaimer, the term of this patent is extended or adjusted under 35 U.S.C. 154(b) by 0 days.

(21) Appl. No.: 17/115,952

(22) Filed: Dec. 9, 2020

(51) Int. Cl.
*A01H 5/12* (2018.01)
*A01H 6/18* (2018.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — Cassandra Bright

(57) ABSTRACT

A new and distinct variety of *Begonia rex-cultorum* plant named 'BDICP11-0' is disclosed, characterized by a large foliage with a strongly spiraling leaf base. Foliage is deeply lobed and serrate and colored greyed-green with a dark center colored both greyed-purple and dark greyed-green. Plants are large and grow rapidly. The new variety is a *Begonia*, and is normally used as an ornamental garden or container plant.

1 Drawing Sheet

Latin name of the genus and species: *Begonia rex-cultorum.*

Variety denomination: 'BDICP11-0'.

BACKGROUND OF THE INVENTION

The new cultivar is the product of a planned breeding program. The new variety originated as the result of a cross performed during 2018 of an unnamed, unpatented proprietary *Begonia rex-cultorum*, as the seed parent and *Begonia rex-cultorum* 'New York Swirl', U.S. Plant Pat. No. 11,948 as the pollen parent. The selection of the new variety was made during August of 2018 by the inventor at a research greenhouse located in Wales, UK.

Asexual reproduction of the new cultivar 'BDICP11-0' was first performed at a research greenhouse located in Wales, UK by terminal vegetative cuttings in August of 2018. 'BDICP11-0' has since produced three generations by vegetative cuttings and has shown that the unique features of this cultivar are stable and reproduced true to type.

SUMMARY OF THE INVENTION

The cultivar 'BDICP11-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BDICP11-0'. These characteristics in combination distinguish 'BDICP11-0' as a new and distinct *Begonia rex-cultorum* cultivar:

1. Large foliage.
2. Spiraling (strongly overlapping cordate) leaf base.
3. Rapid growth.
4. Deeply lobed and serrate leaf margin.

5. Greyed-Green foliage with a dark center colored both greyed-purple and dark greyed-green.

PARENT COMPARISON

Plants of the new cultivar 'BDICP11-0' are similar to plants of the seed parent variety in most horticultural characteristics. However, plants of the new cultivar 'BDICP11-0' differ in the following:

1. Leaves of the new variety are larger than leaves of the seed parent.
2. Plants of the new variety are larger than plants of the seed parent.
3. Foliage of the new variety has a spiraling base not found in the seed parent.

Plants of the new cultivar 'BDICP11-0' are similar to plants of the pollen parent variety in most horticultural characteristics. However, plants of the new cultivar 'BDICP11-0' differ in the following:

1. Leaves of the new variety are much more deeply lobed, than foliage of the pollen parent.
2. Plants of the new variety are larger than plants of the pollen parent.
3. Foliage of the new variety has a thicker dark margin.

COMMERCIAL COMPARISON

Plants of the new cultivar 'BDICP11-0' are similar to plants of the commercial variety, *Begonia* 'BRXBR15-0', U.S. Plant Pat. No. 24,110 in most horticultural characteristics. Plants of the new cultivar 'BDICP11-0' differ in the following:

1. Foliage of the new variety has a jagged margin not found on 'Rothko'.
2. Foliage of the new variety is greyed-green with a dark center, foliage of 'Rothko' is red with black margins.
3. Foliage of the new variety has a strongly spiraling base, a characteristic not found in 'Rothko'.

Plants of the new cultivar 'BDICP11-0' are similar to plants of the commercial variety, *Begonia* 'Bewitched White' unpatented, in most horticultural characteristics. However, plants of the new cultivar 'BDICP11-0' differ in the following:

1. Foliage of the new variety has a strongly spiraling base, a characteristic not found in this comparator.
2. Foliage of the new variety has a dark center not found on 'Bewitched White'.

BRIEF DESCRIPTION OF THE PHOTOGRAPH

The present invention of a new and distinct variety of *Begonia* is shown in the accompanying photographs, the colors being as nearly true as possible with color photographs of this type. Age of the plant is approximately 16 weeks, shown in a 1 gallon pot.

DETAILED BOTANICAL DESCRIPTION

In the following description, color references are made to The Royal Horticultural Society Colour Chart 2007 except where general terms of ordinary dictionary significance are used. The following observations and measurements describe 'BDICP11-0' plants grown in a commercial controlled greenhouse in Santa Paula, Calif. Measurements and numerical values represent averages of typical plant types.

Botanical classification: *Begonia rex-cultorum* 'BDICP11-0'.

Age of plant described: Approximately 12 weeks.

Container of plant described: 6-inch pot.

Propagation:

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with the R.H.S. chart.

Plant:

Growth habit: Upright and outwardly growing, fleshy annual.

Plant shape: Globular.

Pot size of plant described: 6-inch.

Height: Approximately 32 cm.

Plant spread: Approximately 42 cm.

Growth rate: Rapid.

Branching characteristics: Basally emerging foliage, no actual branches, only petioles.

Foliage:

*Type*.—Single, basally emerging foliage and long petioles.

*Orientation*.—Mainly upwardly facing foliage. Lower, oldest foliage outwardly facing.

*Strength*.—Very strong, hard foliage, resists breakage.

*Texture, top surface*.—Sparsely hirsute.

*Texture lower surface*.—Main surface non-pubescent, veins sparsely hirsute. Largest veins more densely hirsute.

*Appearance*.—Metallic, matte and slightly leathery appearance to upper surface. Lower surface matte.

*Quantity*.—Approximately 25 to 30.

*Shape of blade*.—Overall orbicular to broad palmate.

*Apex*.—Acute.

*Base*.—Spiraling.

*Margin*.—Incised and serrate. Sinuses acute, average depth approximately 1.0 to 2.8 cm.

*Aspect*.—Mainly flat, slight upward fold.

*Mature leaves*.—

*Average length*.—Average range 18 to 22 cm.

*Average width*.—Average range 18 to 22 cm.

*Color*.—Mature foliage upper side: Main color near Greyed-Green 191C. Center blotch, approximately 30% of leaf blade RHS Greyed-Purple N186D. From this center blotch Greyed-Green N189A thick streaks along veins emerge. Well defined thin margin about 5 to 10 mm colored near Greyed-Purple 186A and 187A. Mature foliage under side: Main color near Greyed-Green 191B. Faint center blotch, approximately 5% to 10% of leaf blade RHS Greyed-Purple 187A. Well defined thin margin about 5 to 10 mm colored near Greyed-Purple 186A and 187D. Venation: Type: Palmate. Venation color upper side: Near Greyed-Purple 187A. Venation color under side: Near Greyed-Purple 183B.

*Petiole*.—Length: Average range 10 to 12 cm. Diameter: Approximately 6 to 8 mm. Color: Background color near RHS Greyed-Purple 183D. Texture: Hirsute.

*Stipule description*.—Length: Approximately 0.8 cm. Diameter: Approximately 0.8 cm. Shape: Deltate. Apex: Acute. Base: Truncate. Color: Immature near RHS Greyed-Purple 185A, upper and lower surfaces. Dries to Grey-Brown 199B, upper and lower surfaces, before leaf matures. Texture: Upper Surface: Very sparsely pilose. Lower Surface: Glabrous.

Flower: Not observed to date.

Reproductive organs: Not observed to date.

Other characteristics:

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

What is claimed is:

1. A new and distinct cultivar of *Begonia rex-cultorum* plant named 'BDICP11-0' as herein illustrated and described.

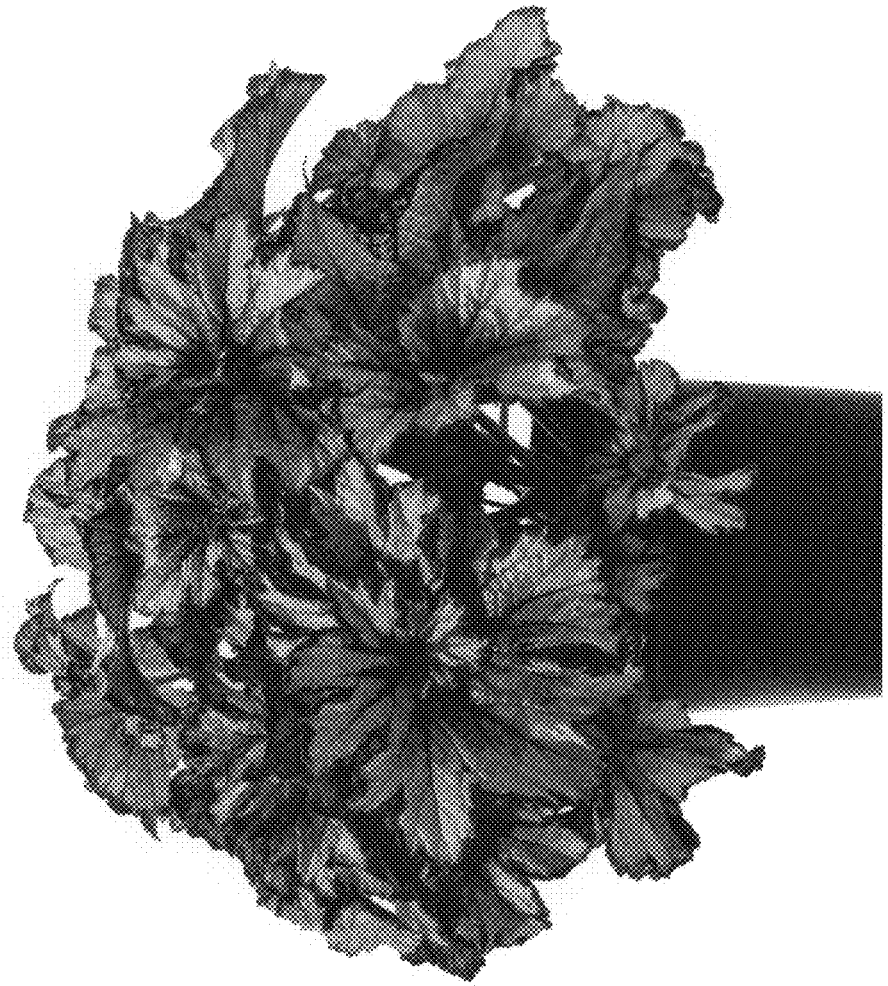

* * * * *